United States Patent [19]

Fozzard

[11] 4,019,965
[45] Apr. 26, 1977

[54] SEPARATION OF PHENOL, CYCLOHEXANONE, AND CYCLOHEXYLBENZENE CONTAINING MIXTURES EMPLOYING DIALKYL AND DICYCLOALKYL PHTHALATES

[75] Inventor: George B. Fozzard, Bartlesville, Okla.

[73] Assignee: Phillips Petroleum Company, Bartlesville, Okla.

[22] Filed: July 20, 1976

[21] Appl. No.: 706,993

[52] U.S. Cl. .................................. 203/60; 203/51; 260/586 P; 260/621 C; 260/621 A
[51] Int. Cl.² ................... B01D 3/40; C07C 39/04; C07C 49/30
[58] Field of Search .................. 203/60, 64, 57, 51, 203/56; 260/586 P, 586 AB, 586 R, 621 A, 621 G, 621 C

[56] References Cited

UNITED STATES PATENTS

| | | | |
|---|---|---|---|
| 2,171,795 | 9/1939 | Kautter | 203/60 |
| 2,762,760 | 9/1956 | Walker | 260/621 A |
| 2,986,583 | 5/1961 | Robbers et al. | 260/621 A |
| 3,169,101 | 2/1965 | Berthoux | 203/64 |
| 3,284,320 | 11/1966 | Fannin et al. | 203/60 |
| 3,492,362 | 1/1970 | Nettesheim | 203/60 |
| 3,630,855 | 12/1971 | Turbin | 260/621 A |

*Primary Examiner*—Wilbur L. Bascomb, Jr

[57] ABSTRACT

Phenol, cyclohexanone, and cyclohexylbenzene containing mixtures are extractively distilled to provide overhead of cyclohexylbenzene and cyclohexanone and a kettle product substantially free of cyclohexylbenzene by employing a dialkyl and/or a dicycloalkyl phthalate. Co-agents or modifiers, e.g., sulfolane, polyalkylene glycols, etc., are advantageously used in some instances.

4 Claims, No Drawings

SEPARATION OF PHENOL, CYCLOHEXANONE, AND CYCLOHEXYLBENZENE CONTAINING MIXTURES EMPLOYING DIALKYL AND DICYCLOALKYL PHTHALATES

This invention relates to the separation of phenol from its azeotropes, including phenol-cyclohexanone azeotrope, which may be in presence of cyclohexylbenzene. In one of its aspects the invention relates to the recovery of phenol and cyclohexanone from the cleavage products resulting from cleavage of the oxidation product of cyclohexylbenzene to provide cyclohexylbenzene hydroperoxide which then is converted to produce the phenol, cyclohexanone, and any unreacted cyclohexylbenzene.

In one of its concepts the invention provides a process for extractive distillation of a mixture containing phenol and cyclohexanone employing as an agent a dialkyl and/or a dicycloalkyl phthalate. In another of its concepts the invention provides such a process in which a co-agent or modifier such as sulfolane and/or a polyether or polyalkylene glycol, e.g., dimethyl triethylene glycol, monomethyl diethylene glycol, etc., is employed.

In a further concept of the invention the extractive distillation yields an overhead product containing essentially cyclohexanone and cyclohexylbenzene. This overhead product is readily separated by fractionation. The extract contains phenol, some cyclohexanone and the agent or solvent. The extract is further separated by stripping and fractionation or, indeed, by extractive distillation to recover a phenol product and additional cyclohexanone.

It is an object of this invention to separate mixtures containing phenol and cyclohexanone which also can contain cyclohexylbenzene. It is another object of this invention to provide an extractive distillation agent or solvent to separate mixtures as described herein. It is a still further object of the invention to provide an extractive distillation operation comprising a mixture of one or more agents or solvents also as described here.

Other aspects, concepts, objects and the several advantages of the invention are apparent from a study of this disclosure and appended claims.

According to the present invention a mixture containing phenol and cyclohexanone, which may contain cyclohexylbenzene, is extractively distilled and thus separated to produce as an overhead product a fraction containing essentially cyclohexanone and when cyclohexylbenzene is present in the mixture being treated some cyclohexylbenzene.

Solvents useful for the invention are the dialkyl and dicycloalkyl phthalates of the general formula

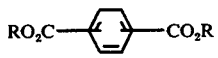

where R can be an alkyl group containing 1–12 carbon atoms. Representative examples include dimethyl, dibutyl, diisobutyl, di(2-ethylhexyl) and didecyl phthalates. R can also be a cycloalkyl group. Representative examples of this class include dicyclohexyl, bis(2-cyclohexylethyl), and bis(4-butyl-cyclohexyl) phthalates. The esters used can be the ortho-, meta-, or paraisomers or mixtures thereof.

In the following examples, Examples 1, 3, and 4 employed dibutyl phthalate, di(2-ethylhexyl) phthalate and dibutyl phthalate, respectively. Example 2 relates that essentially no separation of the azeotropic mixture was achieved employing a partially hydrogenated terphenyl as selective solvent. Extractive distillations according to the concept of the invention were conducted in a ¾-inch diameter packed column 3 feet long.

EXAMPLE 1

A 70–30 weight percent mixture of phenol-cyclohexanone, which is an azeotropic mixture boiling at 122° C at 100 mm Hg absolute pressure, was fed to the column near the mid-point at a rate of 1.5 cc/min at a temperature of 125° C. Column operating pressure was 50 mm Hg absolute. Dibutyl phthalate solvent was fed near the top of the column at a rate of 1.2 cc/min at a temperature of 138° C. Overhead product was taken off at an average rate of 0.4 cc/min and a purity of 90 percent cyclohexanone with no detectable dibutyl phthalate. Accumulated kettle product was 95 percent phenol on a solvent-free basis.

EXAMPLE 2

A 70–30 weight percent mixture of phenol-cyclohexanone was subjected to extractive distillation in a similar manner using Monsanto's HB-40, a partially hydrogenated terphenyl, as the selective solvent. Essentially no separation of the azeotropic mixture was achieved.

EXAMPLE 3

A 70–30 weight percent mixture of phenol-cyclohexanone was subjected to extractive distillation at 50 mm Hg absolute pressure with about 3.7 cc/mm of di(2-ethylhexyl) phthalate using a feed rate of 1.8 cc/min of the azeotropic mixture. Overhead product purity was 95 percent cyclohexanone and kettle product was 93 percent phenol on a solvent-free basis.

EXAMPLE 4

A mixture composed of 46 percent phenol, 23 percent cyclohexanone and 31 percent cyclohexylbenzene was fed into the mid-point of the extractive distillation column operating at 50 mm Hg absolute pressure at a rate of 1.2 cc/min and a temperature of 145° C. Dibutyl phthalate solvent was introduced near the top of the column at a rate of 2.1 cc/min and a temperature of 88° C. Overhead product composition was typically about 89 percent cyclohexanone, 11 percent cyclohexylbenzene and only about 0.01 percent phenol. Accumulated kettle product was about 20 percent cyclohexanone, 80 percent phenol and only 0.08 percent cyclohexylbenzene.

The process of the invention as applied to the cleavage product resulting from the cleavage of an organic hydroperoxide e.g. cyclohexylbenzene hydroperoxide, of the cleavage product containing phenol, cyclohexanone and unreacted cyclohexylbenzene can include fractionation to separate 90 to 95 percent, approximately, of the unconverted cyclohexylbenzene, extractive distillation with a solvent or agent according to the invention, thus breaking the azeotrope, fractionation of the overhead product from the extractive distillation to recover purified cyclohexanone on the one hand and cyclohexylbenzene on the other, a stripping of the extractive distillation kettle product to recover solvent for recycle and, finally, separating the recovered phenol by azeotropic distillation or in a second extractive distillation.

The problem to which this invention applies neatly as illustrated in the following:

Oxidation and cleavage of cyclohexylbenzene (CHB) provides a product mixture of phenol (Bp 182° C), cyclohexanone (Bp 156° C), and cyclohexylbenzene (Bp 238° C). Careful fractionation, however, does not provide a mixture of phenol and cyclohexanone free of CHB. The CHB appears to be carried over with the phenol-cyclohexanone azeotrope to the extent of 2 to 5 percent of the overhead product. Mixtures of phenol and CHB are not separated cleanly by fractionation, but mixtures of CHB and cyclohexanone are. Extractive distillation of a mixture of phenol, cyclohexanone, and CHB with a solvent of the invention, e.g. di(2-ethylhexyl) phthalate, provides an overhead cyclohexanone product of high purity with phenol and CHB down to the kettle.

Reasonable variation and modification are possible within the scope of the foregoing disclosure and the appended claims to the invention the essence of which is that it has been found that extractive distillation of mixtures of phenol, cyclohexanone, and cyclohexylbenzene with a solvent as herein described i.e., a dialkyl or a dicycloalkyl phthalate, with or without a modifier, can provide an overhead product essentially composed of cyclohexanone and cyclohexylbenzene, which are readily separated, and the kettle product essentially free of cyclohexylbenzene containing good purity phenol.

I claim:
1. An extractive distillation of a mixture containing phenol and cyclohexanone, which mixture may contain cyclohexylbenzene which comprises employing as a solvent at least one of dialkyl and a dicycloalkyl phthalate.
2. A process according to claim 1 wherein the solvent employed has the general formula

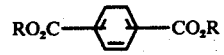

where R can be an alkyl group containing 1–12 carbon atoms.
3. A process according to claim 1 wherein the solvent is selected to be at least one of the following: dimethyl, dibutyl, diisobutyl, di(2-ethylhexyl), didecyl, dicyclohexyl, bis(2-cyclohexylethyl), and bis(4-butylcylohexyl) phthalates and isomers of the esters.
4. A process according to claim 1 wherein there is recovered as an overhead product cyclohexanone, containing cyclohexylbenzene when present, the kettle product is stripped to recover solvent and then subjected to an azeotropic or second extractive distillation to recover phenol.

* * * * *